United States Patent [19]

Karami

[11] 4,055,180

[45] Oct. 25, 1977

[54] ABSORBENT ARTICLE WITH RETAINED HYDROCOLLOID MATERIAL

[75] Inventor: Hamzeh Karami, Crystal Lake, Ill.

[73] Assignee: Colgate-Palmolive Company, New York, N.Y.

[21] Appl. No.: 679,541

[22] Filed: Apr. 23, 1976

[51] Int. Cl.² .................. A41B 13/02; A61F 13/16
[52] U.S. Cl. .................. 128/287; 128/284; 128/290 P; 128/296
[58] Field of Search .................. 128/284, 287, 290 R, 128/290 P, 296

[56] References Cited

U.S. PATENT DOCUMENTS

| 3,221,738 | 12/1965 | Ekberg et al. | 128/287 |
| 3,344,789 | 10/1967 | Arnold et al. | 128/287 |
| 3,528,421 | 9/1970 | Vaillancourt | 128/284 |
| 3,645,264 | 2/1972 | Gallagher | 128/296 |
| 3,670,731 | 6/1972 | Harmon | 128/284 |
| 3,762,415 | 10/1973 | Morrison | 128/290 |
| 3,881,491 | 5/1975 | Whyte | 128/287 |
| 3,888,256 | 6/1975 | Studinger | 128/296 |
| 3,890,974 | 6/1975 | Kozak | 128/287 |
| 3,903,889 | 9/1975 | Torr | 128/287 |
| 3,965,906 | 6/1976 | Karami | 128/287 |

Primary Examiner—Aldrich F. Medbery
Attorney, Agent, or Firm—Powell L. Sprunger

[57] ABSTRACT

An absorbent article comprising, an absorbent pad assembly having an absorbent pad, and pockets for retaining a hydrocolloid material in association with the pad.

31 Claims, 13 Drawing Figures

ABSORBENT ARTICLE WITH RETAINED HYDROCOLLOID MATERIAL

BACKGROUND OF THE INVENTION

The present invention relates to absorbent articles.

A various assortment of absorbent articles, such as disposable diapers and sanitary napkins, have been proposed for absorbing and retaining body fluids. Such articles have been constructed with an absorbent pad having a relatively large volume of pad material, in order to provide the necessary absorbency and fluid holding capacity for the articles, which add an undesired bulk to the articles. For example, disposable diapers are commonly made from a fluid impervious backing sheet, a fluid pervious cover sheet, and an absorbent pad, such as comminuted wood pulp known in the art as wood fluff, located between the backing and cover sheets. The pads of such conventional diapers are relatively bulky, particularly in the crotch region, resulting in a poor fit and minimal comfort to the infant.

More recently, it has been proposed to include highly absorbent materials, such as hydrocolloid polymers, in the pads. In theory, the hydrocolloid materials permit a reduction in pad bulk while increasing desirable absorbent and fluid holding characteristics of the pads, since such materials are capable of absorbing and retaining many times their weight in liquid, such as urine or other body fluids. In practice, use of such materials in absorbent articles has been limited due to numerous difficulties caused by the nature of the materials.

Initially, it is preferred that the hydrocolloid materials be utilized in a particulate form, such as granules or flakes, since the particles provide a greater exposed surface area for increased absorbency. However, it has been found that when placed in the pad, the particles migrate in the pad before the article has been used by the wearer. Particle migration may take place during packaging, storage, transportation, or other handling of the articles, and results in movement of the particles from their initial location to remote parts of the pad where they are less effective.

When wetted, the hydrocolloid materials swell and become gelatinous, and assume a slippery or slimy texture which is unstable. As a result, the materials migrate further in the pad when wetted, and cause the pad to become unstable. Thus, it has been found that the wetted materials cause the pads to shift, ball, split and shred during use of the articles. Further, certain of the wetted hydrocolloid materials may be somewhat irritating to the skin, and it is thus desirable to minimize contact of the materials with the skin.

SUMMARY OF THE INVENTION

A principal feature of the present invention is the provision of an absorbent article which retains a hydrocolloid material at a fixed location for improved performance of the article.

The article of the present invention comprises an absorbent pad assembly having an absorbent pad, and a first retaining sheet. The sheet is attached to the pad or a second retaining sheet in areas and is free of attachment in regions between the areas to define pocket means. The pad assembly has a hydrocolloid material positioned in the pocket means.

A feature of the invention is that the retaining sheet prevents migration of the hydrocolloid material prior to and during use of the article.

Another feature of the present invention is that the hydrocolloid material is retained at a desired location in the article to provide maximum absorbency and fluid retention during use of the article.

A further feature of the invention is that the article prevents movement of the hydrocolloid material into the absorbent pad during use of the article, and thus prevents degradation of the pad by the wetted hydrocolloid material.

Still another feature of the invention is that the article prevents contact of the wetted hydrocolloid material against the wearer's skin.

Further features will become more fully apparent in the following description of the embodiments of this invention and from the appended claims.

DESCRIPTION OF THE PREFERRED EMBODIMENTS

Figure 1:
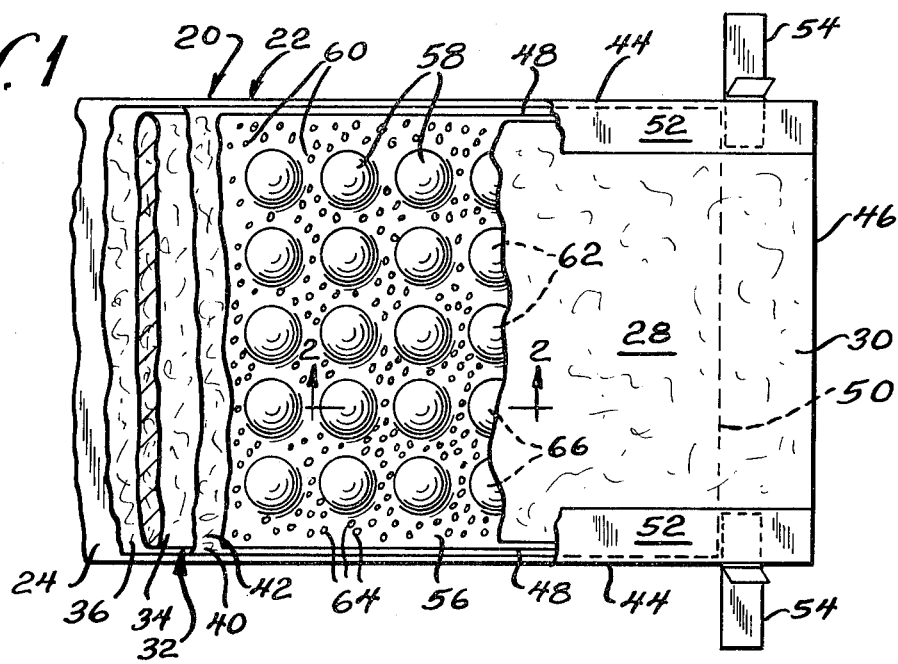
FIG. 1 is a fragmentary plan view of an absorbent article of the present invention, shown in the form of a disposable diaper.
Figure 2:
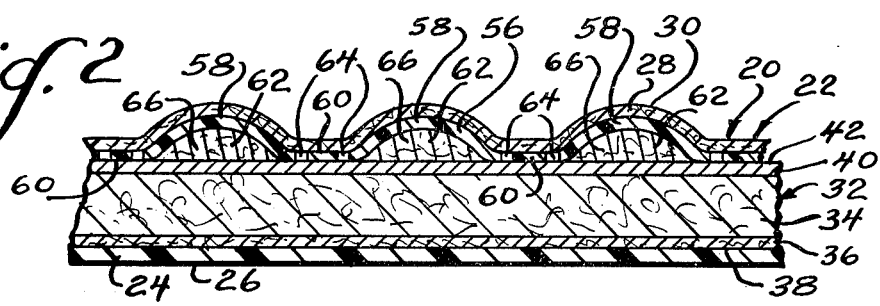
FIG. 2 is a fragmentary sectional view taken substantially as indicated along the line 2—2 of FIG. 1.

Referring now to FIGS. 1 and 2, there is shown an absorbent article generally designated 20 having an absorbent pad assembly 22. For convenience, the article 20 is disclosed in the form of a disposable diaper, although it will be understood that the invention is applicable to other absorbent articles, such as sanitary pads and maternity napkins.

The pad assembly 22 has a fluid impervious backing sheet 24, such as polyethylene, defining a back surface 26 of the article or diaper, a fluid pervious top or cover sheet 28 defining a front surface 30 for the diaper, and an absorbent pad 32 positioned intermediate the top sheet 28 and backing sheet 24. The absorbent pad 32 may have a pad portion 34 codmprising a cellulosic material, such as one or more sheets of cellulosic wadding or comminuted wood pulp known in the art as wood fluff, a back wadding sheet 36 of cellulosic material defining a back surface 38 of the pad 32, and a front wadding sheet 40 of cellulosic material defining a front surface 42 of the pad 32. The front and back wadding sheets 40 and 36, respectively, provide structural integrity for the pad portion 34 during use of the article.

As illustrated in FIG. 1, the pad assembly 22 has a pair of side edges 44 and end edges 46 connecting the side edges 44, and the absorbent pad 32 has a pair of side edges 48 and end edges 50 connecting the side edges 48. In a preferred form, the side edges 48 of the pad 32 are located adjacent the side edges 44 of the pad assembly 22, and the backing sheet 24 has lateral side margins 52 folded over and secured to the top sheet 28 over lateral side margins of the pad 32. The diaper may have conventional tape fasteners 54 for use in securing the diaper about an infant during placement of the diaper.

Referring to FIGS. 1 and 2, the pad assembly 22 has a fluid impervious retaining sheet 56 positioned intermediate the top sheet 28 and the front wadding sheet 40. The retaining sheet 56 is free of attachment or spaced from the wadding sheet 40 in a plurality of spaced regions 58, and is attached to the front surface 42 of the wadding sheet 40 in areas 60 surrounding the regions 58. Thus, the retaining sheet 56 and wadding sheet 40 define a plurality of spaced pockets 62 located intermediate the retaining sheet 56 and front wadding sheet 40. In the particular embodiment shown, the pockets 62 have a generally circular shape, and are aligned laterally and longitudinally along the pad assembly 22.

Although the retaining sheet 56 may be attached to the front wadding sheet 40 by any suitable means, such as adhesive, in a preferred form the retaining sheet 56 comprises a film of thermoplastic material, such as polyethylene, and the film is fused to the front wadding sheet in the areas 60 by suitable means, such as by heating. As shown, the areas 60 of the retaining sheet or film 56 have a plurality of openings or apertures 64 extending through the sheet 56 to permit passage of body fluids through the openings 64 into the pad 32. Although the openings 64 may be formed in any suitable manner, in one form the openings may comprise perforations in the sheet 56 which are enlarged by heating when the sheet 56 is fused to the pad, in a manner similar to that described in my copending application Ser. No. 552,463, filed Feb. 24, 1975. In the present embodiment, as shown, the retaining sheet 56 is closed in the regions 58 to prevent passage of fluids between the pockets 62 and the front surface 30 of the pad assembly 22.

The pad assembly 22 has a hydrocolloid material 66, such as (a) hydrolyzed starch polyacrylonitrile copolymer H-span, Product 35-A-100, Grain Processing Corp., Muscatine, Iowa, disclosed in U.S. Pat. No. 3,661,815, (b) Product No. XD-8587.01L, which is cross-linked, Dow Corning Chemcial Co., Midland, Michigan, (c) Product No. SGP 502S, General Mills Chemical, Inc., Minneapolis, Minnesota, (d) Product No. 78-3710, National Starch and Chemical Corp., New York, N.Y, (e) a hydrogel base product, Carbowax, a trademark of Union Carbide Corp., Charleston, West Virginia, or (f) base-saponisied starch-polyacrylonitrile and graft copolymers, United States Department of Agriculture, Peoria, Illinois, disclosed in U.S. Pat. No. 3,425,971, which is positioned in the pockets 62. Such hydrocolloid materials have the capability of absorbing many times their weight in liquids such as urine or other body fluids, and swell and form a gelatinous mass when wetted. In general, the hydrocolloid materials useful in the articles of the present invention may be organic or inorganic, are physiologically nonobjectionable (nontoxic), and are characterized by swelling in the presence of water, by a relatively high affinity for water, and by normally at least partially assuming a suspension in the presence of water. Preferably, the hydrocolloid materials are utilized in a particulate form, such as powders, granules, or flakes, although they may be coated on one or more of the sheets in a solution, if desired.

The retaining sheet 56 and front wadding sheet 40 retain the hydrocolloid materials 66 in the pockets 62, and prevent migration of the materials 66 into and throughout the pad portion 34 during transportation, storage, or other handling of the articles prior to use. Thus, the materials 66 are retained at desired locations in the pad assembly 22 for maximum benefit during use, and are prevented from passing to undesired locations in the pad assembly prior to use of the article.

Figure 4:
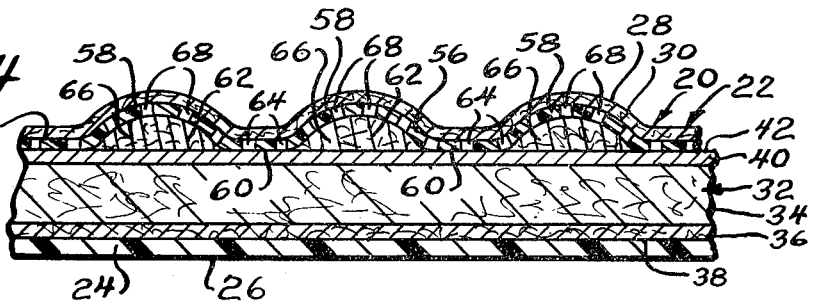
FIG. 4 is a fragmentary sectional view of another embodiment of the article of the present invention.

During use of the article or diaper 20, body fluids pass through the openings 64 of the retaining sheet areas 60 and into the pad 32, after which the body fluids are permitted to pass through the front wadding sheet 40 into the pockets 62 for absorption and retention by the hydrocolloid materials 66. The front wadding sheet 40 has a sufficient wet strength to prevent passage of the wetted hydrocolloid material 66 through the wadding sheet 40 into the pad portion 34, such that the wadding sheet 40 serves as a second retaining sheet to retain the wetted materials in the pockets during use of the article. Additionally, the wetted materials 66 are prevented from entering the pad portion 34 to eliminate degradation of the pad, such as shifting, balling, splitting, or shredding of the pad portion 34, which otherwise might occur due to the unstable and slippery texture of the wetted materials 66. Moreover, the closed regions 58 of the retaining sheet 56 prevent passage of the wetted materials 66 to the front surface of the pad assembly, and thus prevent contact of the wetted materials against the wearers's skin. However, if desired, the regions 58 of the retaining sheet 56 may have relatively small openings or apertures 68, as shown in FIG. 4, by maintaining the size of the openings 68 smaller than the size of the hydrocolloid particles. Thus, the openings 68 permit passage of body fluids into the pockets 62, but are sufficiently small to prevent passage of the wetted materials to the front surface of the article. In this regard, it is noted that the particles swell when wetted, further limiting the possibility of passage of the particles through the openins 68. Although the retaining sheet 56 has been described as being attached to the front surface of the pad, it will be appreciated that the sheet may be attached to the back surface of the pad, or to a surface of a pad layer, if desired.

Figure 3:
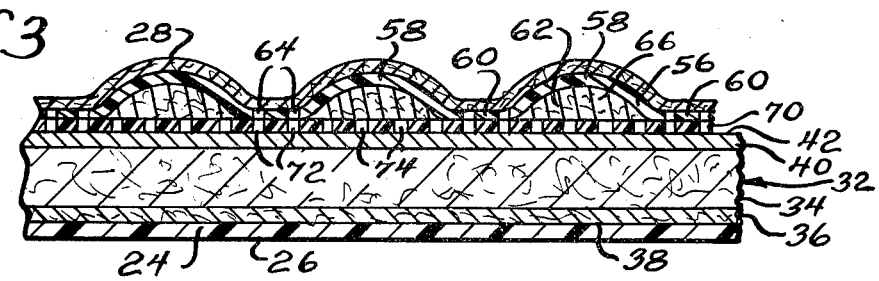
FIG. 3 is a fragmentary sectional view of another embodiment of the article of the present invention.

Another embodiment of the present invention is illustrated in FIG. 3, in which like reference numerals designate like parts. In this embodiment, the pad assembly 22 has a second retaining sheet 70 attached to the first retaining sheet 56 in the areas 60, and defining pockets 62 in the regions 58, such that the hydrocolloid material 66 is retained in the pockets 62 intermediate the retaining sheets 56 and 70. In a preferred form, the second retaining sheet 70 comprises a fluid impervious material, such as polyethylene, and has a plurality of openings 72 aligned with the opening 64 of the first retaining sheet 56 to permit passage of body fluids through the retaining sheets 56 and 70. The second retaining sheet 70 also has a plurality of openings 74 in the regions 58 to permit passage of body fluids into the pockets 62. Thus, in the embodiment shown, the second retaining sheet 70 is positioned adjacent the front surface 42 of the pad 32, such that body fluids pass through the openings 64 and 72 of the retaining sheets 56 and 70, respectively, into the pad during use of the article, and from the pad 32 through the openings 74 of the sheet 70 into the pockets 62 for absorption and retention by the hydrocolloid materials 66. As before, the materials 66 are retained in the pockets 62 before and during use of the article. In this regard, the size of the openings 74 is preferably less than the size of the hydrocolloid particles 66 in the pockets 62.

If desired, the second retaining sheet 70 may comprise a cellulosic sheet additional to the wadding sheet, with sufficient wet strength to prevent passage of the wetted hydrocolloid materials 66 through the sheet 70, or the sheet 70 may be arranged with the top wadding sheet 40 to prevent passage of such wetted materials. In a preferred form, at least one of the first and second retaining sheets 56 and 70 comprises a film of thermoplastic material, and the sheets are fused together in the areas 60. If desired, the first and second retaining sheets 56 and 70 may be located intermediate the backing sheet 24 and the back surface 38 of the pad 32, or may be positioned intermediate layers of absorbent pads.

Figure 5:
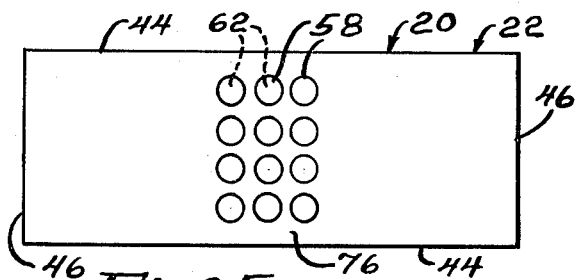
FIG. 5 is a diagrammatic plan view showing an embodiment of the article of the present invention.
Figure 6:
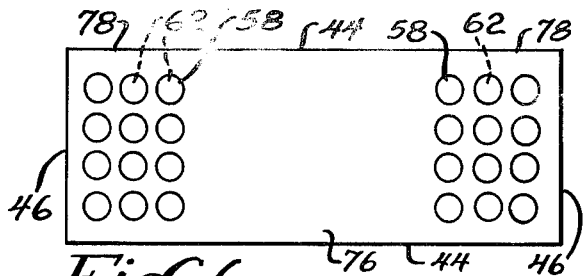
FIG. 6 is a diagrammatic plan view showing an embodiment of the article of the present invention.
Figure 7:
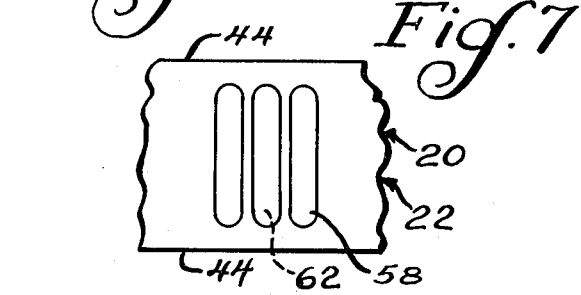
FIG. 7 is a diagrammatic fragmentary plan view showing an embodiment of the article of the present invention.
Figure 8:
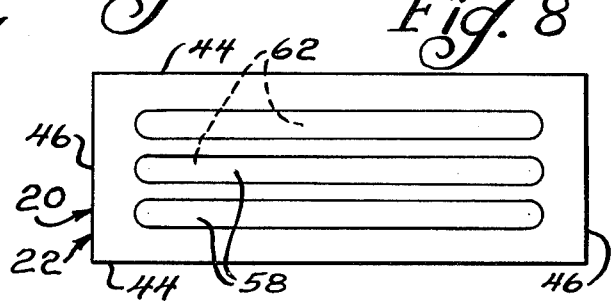
FIG. 8 is a diagrammatic plan view showing an embodiment of the article of the present invention.

A diagrammatic view showing an arrangement of the article pockets is set forth in FIG. 5. In this embodiment, the regions 58 and pockets 62 retaining the hydrocolloid materials have a generally circular shape and are arranged in rows in a longitudinal central portion of the article 20 between the end edges 46. For example, in a disposable diaper, the pockets 62 may be located in a crotch region 76 at the point of contact of body fluids during use of the diaper. However, as shown in FIG. 6, if desired the pockets 62 may be arranged adjacent the end edges 46 of the article, for example, in waistline portions 78 of a disposable diaper. In an alternative form, as shown in FIG. 7, the pockets 62 and regions 58 may be elongated, and may extend laterally between the side edges 44 of the article 20. In a further form, as shown in FIG. 8, the elongated regions 58 and pockets 62 may extend longitudinally between the end edges 46 of the article 20.

Figure 9:
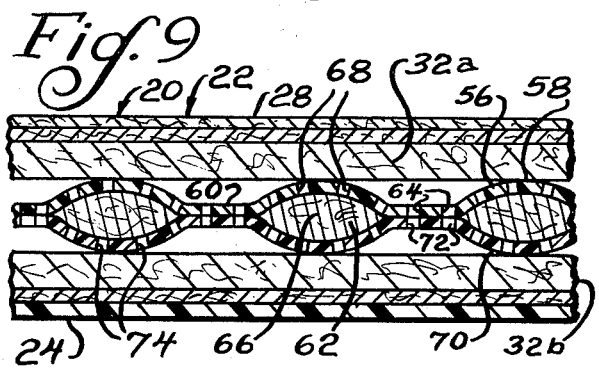
FIG. 9 is a fragmentary sectional view of another embodiment of the article of the present invention.

Another embodiment of the article 20 of the present invention is illustrated in FIG. 9, in which like reference numerals designate like parts. In this embodiment, the pad assembly 22 has first and second layers 32a and 32b of absorbent pads, and first and second retaining sheets 56 and 70 positioned intermediate the pads 32a and b. The sheets 56 and 70 are preferably made from a fluid impervious material, such as polyethylene, and are attached together in the areas 60, such as by fusing, while being spaced in the regions 58 or otherwise defining pockets 62 intermediate the retaining sheets 56 and 70. The sheets 56 and 70 have aligned openings 64 and 72 to permit passage of body fluids through the sheets 56 and 70 in the areas 60. The retaining sheet 56 has a plurality of openings 68 in the regions 58 to permit passage of body fluids from the pad 32a into the pockets 62, while the retaining sheet 70 has a plurality of openings 74 in the regions 58 to permit passage of body fluids from the pad 32b into the pockets 62. Thus, the sheets 56 and 70 permit passage of body fluids between the pads 32a and 32b, and permit passage of body fluids from both of the pads 32a and b into the pockets 62 for absorption and retention by the hydrocolloid materials in the pockets 62. As before, the size of the openings 68 and 74 are preferably smaller than the size of the hydrocolloid particles to minimize possiblility of particle passage through the sheets 56 and 70. In an alternative form of the article 20, the apertured retaining sheets 56 and 70 may be positioned intermediate the top or backing sheets and the pad.

Figure 10:
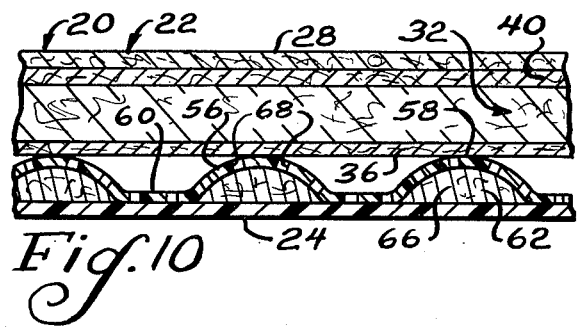
FIG. 10 is a fragmentary sectional view of another embodiment of the article of the present invention.
Figure 12:
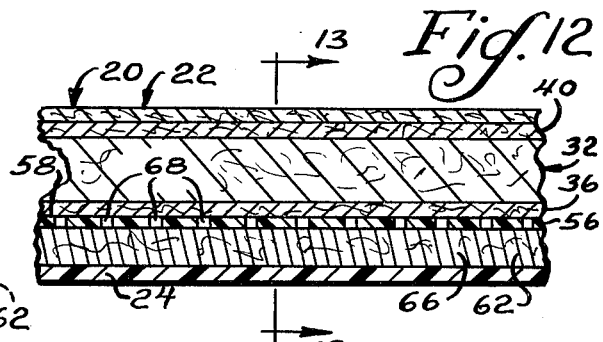
FIG. 12 is a fragmentary sectional view of another embodiment of the article of the present invention.
Figure 13:
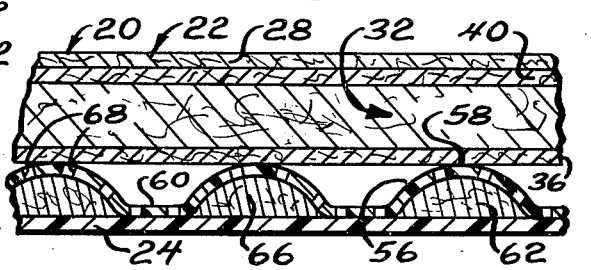
FIG. 13 is a fragmentary sectional view taken substantially as indicated along the line 13—13 of FIG. 12.

Another embodiment of the present invention is illustrated in FIG. 10, in which like reference numerals designate like parts. In this embodiment, the retaining sheet 56 is attached to the inner surface of the backing sheet 24 in the areas 60, while defining pockets 62 in the regions 58. The hydrocolloid material 56 is retained in the pockets 62 defined intermediate the retaining sheet 56 and backing sheet 24 in the regions 58. As shown, the retaining sheet 56, is fluid impervious, has a plurality of openings 68 in the regions 58 to permit passage of body fluids from the pad 32 into the pockets 62 for absorption and retention by the hydrocolloid materials 66. In a preferred form, at least one of the sheets 56 or 24 comprise a film of thermoplastic material, and the sheets 56 and 24 are fused together in the areas 60. In the embodiment of FIG. 10, the regions 58 and pockets 62 may have a generally circular shape, as previously described, although they may have any suitable shape, as desired, such as relatively elongated pockets and regions, as shown in FIGS. 12 and 13.

Figure 11:
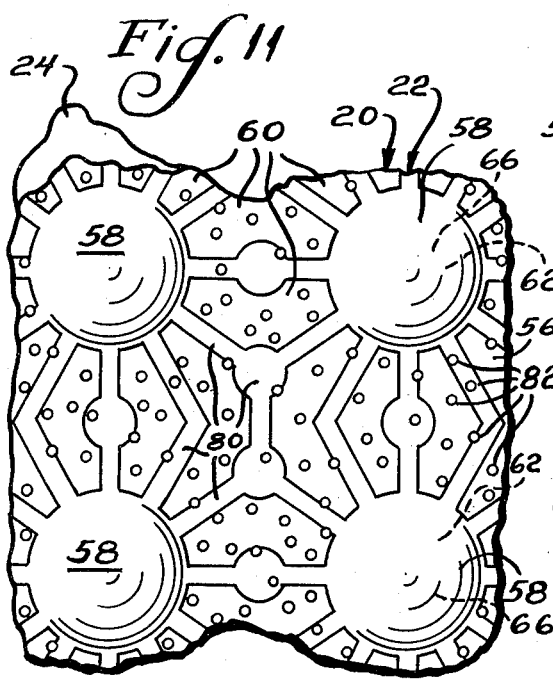
FIG. 11 is a fragmentary plan view showing a retaining portion in another embodiment of the article of the present invention.

Another embodiment of the article 20 of the present invention is illustrated in FIG. 11, in which like reference numerals designate like parts. In this embodiment, the retaining sheet 56 is attached to the backing sheet 24, such as by fusing the sheets together, in areas of attachemet 60. The retaining sheets 56 and 24 define pockets 62 in regions 58 for retaining the hydrocolloid materials intermediate the retaining sheet 56 and backing sheet 24. The retaining sheet 56 and backing sheet 24 are free of attachment at locations defining channel means 80 extending between the sheets 56 and 24 and communicating with the pockets 62. As shown, the retaining sheet 56 has a plurality of openings 82 extending through the sheet 56, with at least a portion of the openings 82 communicating with the network of channel means 80. In this embodiment, the regions 58 of the sheet 56 are closed to prevent passage of body fluids through the sheet 56 in the regions 58. However, the body fluids are permitted to pass through the openings 82 into the channel means 80, after which the body fluids pass through the channel means 80 into the pockets 62 for absorption and retention by the hydrocolloid materials retained in the pockets. In an alternative form, the openings 82 may extend through the joined sheets, and the sheets may be positioned adjacent a front surface of the pad, or may be located intermediate separate layers of the pad.

The foregoing detailed description is given for clearness of understanding only, and no unnecessary limitations should be understood therefrom, as modifications will be obvious to those skilled in the art.

I claim:

1. An absorbent article comprising, a fluid pervious top sheet, a fluid impervious backing sheet, first and second retaining sheets located intermediate said top and backing sheets and extending substantially between opposed ends of the article, said retaining sheets being attached together in areas and defining a plurality of pockets between said areas and means for permitting passage of body fluids into the pockets, and a hydrocolloid material positioned in said pockets.

2. An absorbent article comprising, a layer of absorbent pad having opposed surfaces, a pair of side edges, and a pair of end edges, first and second retaining sheets positioned adjacent one of said surfaces of said layer including a longitudinal central portion intermediate the end edges, said retaining sheets being attached together in areas and defining a plurality of pockets between said areas and means for permitting passage of body fluids into the pockets, and a hydrocolloid material positioned in said pockets.

3. The article of claim 2 wherein said retaining sheets define a plurality of spaced pockets for said material adjacent at least one of said end edges of the pad.

4. The article of claim 2 wherein said retaining sheets define at least one elongated pocket for said material extending laterally between said side edges.

5. The article of claim 2 wherein said retaining sheets define at least one elongated pocket for said material extending longitudinally between said end edges.

6. The article of claim 2 including a second layer of absorbent pad, and in which said retaining sheets are located intermediate said layers.

7. An absorbent article comprising, a fluid impervious backing sheet, a fluid pervious top sheet, a retaining sheet located intermediate said top and backing sheets, said retaining sheet being attached to said backing sheet in areas including a portion thereof spaced from said top sheet and defining pocket means between said areas intermediate the backing and retaining sheet, with said retaining sheet permitting passage of body fluids into the pocket means, and a hydrocolloid material positioned in said pocket means.

8. An absorbent article comprising, an absorbent pad assembly having an absorbent pad, a fluid impervious retaining sheet located adjacent a front surface of said pad, said retaining sheet being attached to the front surface of the pad in areas surrounding a plurality of regions, with said retaining sheet defining a plurality of spaced pockets between the retaining sheet and pad in said regions, and with said retaining sheet having a plurality of openings extending through said areas to permit passage of body fluids into said pad, and said pad assembly having a hydrocolloid material located in said pockets.

9. The article of claim 8 wherein said pad includes a front wadding sheet defining a front surface of the pad, and in which said areas of the retaining sheet are attached to said wadding sheet.

10. The article of claim 8 wherein said retaining sheet comprises a film of thermoplastic material, and in which said film is fused to said pad in said areas.

11. The article of claim 8 wherein said retaining sheet is closed in said regions to prevent passage of liquid between said pockets and a front surface of the article.

12. The article of claim 8 wherein said retaining sheet has a plurality of openings extending through said regions.

13. The article of claim 12 wherein said hydrocolloid material comprises a plurality of particles, and in which the size of said openings in said regions is smaller than the size of said particles.

14. The article of claim 8 including a fluid pervious cover sheet covering a front surface of said retaining sheet, and a fluid impervious backing sheet covering a back surface of said pad.

15. An absorbent article comprising, an absorbent pad assembly having an absorbent pad, a first fluid impervious retaining sheet located adjacent a front surface of the pad, a second fluid impervious retaining sheet located adjacent a front surface of the first retaining sheet, said first and second sheets being attached in areas surrounding a plurality of regions, with said first and second sheets defining a plurality of spaced pockets in said regions, with said first and second sheets having a plurality of aligned openings in said areas permitting passage of body fluids through the openings into said pad, and with said first sheet having a plurality of openings in said regions permitting passage of fluid from the pad into said pockets, and said pad assembly having a hydrocolloid material in said pockets.

16. The article of claim 15 wherein said second sheet is closed in said regions to prevent passage of fluid between said pockets and a front surface of the article.

17. The article of claim 15 in which at least one of said first and second sheets comprises a film of thermoplastic material, and in which said first and second sheets are fused in said areas.

18. The article of claim 15 including a fluid pervious top sheet covering a front surface of said second sheet, and a fluid impervious backing sheet covering a back surface of said pad.

19. An absorbent article comprising, an absorbent pad assembly having layers of first and second absorbent pads, a first retaining sheet located adjacent an inner surface of said first pad, and a second retaining sheet located intermediate said first sheet and an inner surface of said second pad, said first and second sheets being attached in areas surrounding a plurality of regions, with said first and second sheets defining a plurality of spaced pockets in said regions, with said first and second sheets permitting passage of fluid through said areas and with at least one of said sheets permitting passage of fluid between pockets and a pad, and said pad assembly having a hydrocolloid material in said pockets.

20. The article of claim 19 wherein said first sheet comprises a fluid impervious material having a plurality of openings in said areas.

21. The article of claim 20 wherein said first sheet has a plurality of openings in said regions.

22. The article of claim 19 wherein said first and second sheets comprise a fluid impervious material having a plurality of aligned openings in said areas, with at least one of said sheets having a plurality of openings in said regions.

23. The article of claim 22 wherein the other of said sheets has a plurality of openings in said regions.

24. The article of claim 19 wherein at least one of said first and second sheets comprises a film of thermoplastic material, and in which said film is fused to the other of said sheets in said area, with said film having a plurality of openings in said areas.

25. The article of claim 19 including a fluid pervious top sheet covering an outer surface of one of said pads, and a fluid impervious backing sheet covering an outer surface of the other of said pads.

26. An absorbent article comprising, an absorbent pad assembly having an absorbent pad, a fluid impervious backing sheet, and a retaining sheet located intermediate said backing sheet and pad, said retaining sheet and backing sheet being attached together in areas surrounding a plurality of spaced regions, with said retaining sheet and backing sheet defining a plurality of spaced pockets in said regions and means for permitting passage of fluids into said pockets, and said pad assembly having a hydrocolloid material in said pockets.

27. The article of claim 26 wherein the retaining sheet comprises a fluid impervious material having a plurality of openings in said regions communicating with the pockets.

28. The article of claim 26 in which at least one of said retaining sheet and backing sheet comprises a film of thermoplastic material, and in which said sheets are fused together in said areas.

29. An absorbent article comprising, an absorbent pad assembly having an absorbent pad, a fluid impervious backing sheet, a fluid impervious retaining sheet located intermediate said backing sheet and pad, said backing sheet and retaining sheet being attached together in areas defining a plurality of spaced pockets intermediate the retaining and backing sheets and defining channel means communicating with said pockets, with said retaining sheet being closed in regions covering said pockets, and with said retaining sheet having a plurality of openings communicating with said channel means to permit passage of fluids through the openings and channel means into the pockets, and said pad assembly having a hydrocolloid material positioned in said pockets.

30. The article of claim 29 wherein at least one of said retaining sheet and backing sheet comprises a film of thermoplastic material, and in which said sheets are fused together in said areas.

31. An absorbent article comprising, an absorbent pad assembly having a backing sheet of fluid impervious material, an absorbent pad including a pad portion and a wadding sheet defining a surface of the pad, a separate retaining sheet being attached to said surface to the wadding sheet in areas spaced from the backing sheet and defining pocket means between said areas intermediate the retaining sheet and said wadding sheet surface, and a hydrocolloid material positioned in said pocket means with said wadding sheet separating the hydrocoloid material from said pad portion.

* * * * *